(12) United States Patent
Redmond et al.

(10) Patent No.: US 7,834,328 B2
(45) Date of Patent: Nov. 16, 2010

(54) METHOD AND APPARATUS FOR STERILIZING INTRALUMINAL AND PERCUTANEOUS ACCESS SITES

(76) Inventors: Russell J. Redmond, 1148 N. Fairview Ave., Goleta, CA (US) 93117; Claude Vidal, 5426 San Patricio Dr., Santa Barbara, CA (US) 93111

( * ) Notice: Subject to any disclaimer, the term of this patent is extended or adjusted under 35 U.S.C. 154(b) by 1326 days.

(21) Appl. No.: 11/345,037

(22) Filed: Jan. 31, 2006

(65) Prior Publication Data
US 2007/0176117 A1    Aug. 2, 2007

(51) Int. Cl.
*A61L 2/10* (2006.01)
(52) U.S. Cl. .................. 250/455.11; 422/24

(58) Field of Classification Search .............. None
See application file for complete search history.

(56) References Cited

U.S. PATENT DOCUMENTS

2003/0017073 A1*  1/2003  Eckhardt et al. ............. 422/24
2006/0147339 A1*  7/2006  Hunter et al. ............... 422/24

* cited by examiner

*Primary Examiner*—Elizabeth L McKane (57) ABSTRACT

A method and apparatus for sterilizing access sites such as attachment points for various therapeutic and diagnostic medical devices. More particularly, the invention concerns a sterilization apparatus which includes a substantially UV-C transparent closure cap for closing the access site and a compact, easy to use irradiating apparatus for controllably irradiating the closure cap with UV-C radiation.

5 Claims, 12 Drawing Sheets

UV Energy Required to Inactivate 90% of Organism Listed

| Organism | Energy Required (micro W-sec/cm$^2$) |
|---|---|
| Bacteria | |
| S. enteritidis | 4000 |
| B. megatheium sp. (veg) | 1300 |
| B. megatheium sp. (spores) | 2730 |
| B. paratyphosus | 3200 |
| B. subtilis | 7100 |
| Corynebacterium Diphtheriae | 3370 |
| Eberthelia typhosa | 2140 |
| E. coli | 3000 |
| Micrococcus Candidus | 6050 |
| Neisseria catarrhalis | 4400 |
| Phytomonas tumefaciens | 4400 |
| Proteus vulgaris | 2640 |
| Pseudomonas aeruginosa | 5500 |
| Pseudomonas fluorescens | 3500 |
| S. typhimurium | 8000 |
| Seratia marcescens | 2450 |
| Dysentery bacilli | 2200 |
| Shigella paradysenteriae | 1680 |
| Spirillum rubrum | 4400 |
| Staphylococcus albus | 1840 |
| Staphylococcus aureus | 2600 |
| Streptococcus hemolyticus | 2160 |
| Streptococcus lactis | 6150 |
| Streptococcus viridans | 2000 |
| Salmonella paratyphi-enteric | 3200 |
| Nitric comma (cholera) | 3375 |
| Leprospira canicola (infectious jaundice) | 3150 |
| Viruses | |
| Infectious hepatitis | 5800 |
| Poliovirus poliomyelitis | 3150 |
| Influenza | 3400 |

Example exposure time calculation:

Using a 1500 microWatt/cm$^2$ light for 2 seconds will generate the required 3000 microWatt-sec/cm$^2$ of energy needed to kill 90% of the E. coli organisms.

METHOD AND APPARATUS FOR STERILIZING INTRALUMINAL AND PERCUTANEOUS ACCESS SITES

BACKGROUND OF THE INVENTION

1. Field of the Invention

The present invention relates generally to methods and apparatus for sterilizing access sites. More particularly, the invention concerns a method and apparatus for sterilizing intraluminal and percutaneous access sites using ultraviolet radiation.

2. Discussion of the Prior Art

According to articles published by the Centers for Disease Control, in their Special Issue, 'Emerging Infectious Diseases', Vol. 7, No. 2, March-April 2001; "Nosocomial (hospital-acquired infections) bloodstream infections are a leading cause of death in the United States. Population-based surveillance studies of nosocomial infections in U.S. hospitals indicate a 5% attack rate or incidence of 5 infections per 1,000 patient-days." With the advent of managed care and incentives for outpatient care, hospitals have a concentrated population of seriously ill patients, so rates of nosocomial infections are undoubtedly correspondingly higher.

By way of example, if 35 million patients are admitted each year to the approximately 7,000 acute-care institutions in the United States, the number of nosocomial infections—assuming overall attack rates of 2.5%, 5%, or 10%—would be 875,000, 1.75 million, or 3.5 million, respectively. If 10% of all hospital-acquired infections involve the bloodstream, 87,500, 175,000 or 350,000 patients acquire these life threatening infections each year. These are staggering numbers, especially considering this is a problem that the patients did not have when they entered the hospital.

One of the first interventions that occurs when a patient is admitted into a hospital is the placement of an intravenous access line (IV). This percutaneously-placed IV line gives the caregivers a direct path to the patient's bloodstream via a peripheral vein for rapid administration of fluids, medication or for drawing blood samples. In more serious cases, where direct access to a high blood flow supply is needed, for example, in chemotherapy delivery, temporary kidney dialysis or heart monitoring catheterization, a Central Venous Access Catheter (CVAC or Central Line) is inserted. This line is typically inserted percutaneously into a major branching vessel, frequently the subclavian vein, and then the distal segment of the catheter is directed into the superior vena cava.

Both peripheral and central catheterization procedures create an open pathway or lumen from an external access site into the bloodstream. This intraluminal access site provides an attachment point for various therapeutic or diagnostic medical devices, including, but not limited to, stopcocks, needle-less access sites, IV bags, infusion pumps, drug delivery pumps, kidney dialysis equipment, thermal dilution catheters, and the like. Unfortunately, this access site also provides an entry point for bacterial infections. Therefore, each time the access site is opened to accommodate the attachment of a medical device there is an opportunity for bacteria to enter the catheter lumen and be transferred into the bloodstream.

In addition to the contamination of the catheter lumen via the external access site, bacteria can also enter by the skin puncture and sub-cutaneous tract that is created by the catheter when the IV or CVAC is placed. Bacteria can then find their way down the outside wall of the catheter to its distal end, infecting the tract along the catheter wall as they migrate.

In an attempt to mitigate the serious problems identified in the preceding paragraphs, many prior art IV lines and CVACs use some type of molded plastic fitting at their proximal end terminated with a female Luer-lock or Luer-slip connector. These connectors must be closed by a Luer cap when not in use to prevent access site contamination. Each time the line is to be accessed, the Luer cap must be removed and discarded as it must be assumed that the outside of the Luer cap is contaminated and that once removed it is nearly impossible to prevent the male Luer configuration from touching a contaminated surface. Therefore, standard prior art infection control practice is to always replace the Luer cap whenever the line is accessed. This procedure is not only costly, but the removal and replacement process provides additional chances for bacteria to enter the lumen of the connector.

In some cases, IV access sites have been converted to needle-less access valves, which incorporate an elastomeric seal that can be opened via the tip of a male Luer connector mounted on a syringe or like device. These needle-less access valves are meant to be cleaned with an alcohol saturated swab before the valve is opened by the sterile male Luer tip of a syringe. Unfortunately, compliance with the swabbing procedures can be sporadic as it requires significant time, additional supplies and proper technique.

The thrust of the present invention is to provide a novel method and apparatus for sterilizing intraluminal and percutaneous access sites. In this regard, and by way of background, the germicidal effects of ultra violet (UV) radiation have been known since the late $19^{th}$ century and in recent years the use of UV radiation has gained broad acceptance in the fields of water and air purification and has found some limited use in food processing and medical device sterilization.

UV light consists of high energy photons which occupy the 200 to 400 nanometer wavelengths of the electromagnetic spectrum. This means that UV light emits slightly less energy than soft X-ray radiation, but significantly more than visible light. UV energy does not directly kill pathogens, but rather causes a photochemical reaction within the genetic structure which inhibits the ability of the pathogens to reproduce, therefore, in effect, killing the pathogen.

The amount of energy delivered by UV light is inversely proportional to its wavelength, therefore, the shorter the wavelength, the greater the energy produced. In general, the UV light portion of the spectrum is made up of three segments; UV-A (315-400 nm), used for sun-tanning lamps, UV-B (280-315 nm) and UV-C (200-280 nm). The UV-B and UV-C regions contain wavelengths with the best germicidal action. Studies have shown that the wavelengths most effective in killing microbes are between 250-265 nm. This value corresponds nicely with the light energy output of a typical, commercially available UV-C germicidal lamp which produces most of its energy output in the range of 254 nm.

SUMMARY OF THE INVENTION

It is an object of the present invention to provide a method and apparatus for sterilizing access sites such as attachment points for various therapeutic or diagnostic medical devices, including, stopcocks, needle-less access sites, IV bags, infusion pumps, drug delivery pumps, kidney dialysis equipment, thermal dilution catheters and like devices. More particularly, it is an object of the invention to provide a method and apparatus for sterilizing intraluminal and percutaneous access sites using ultraviolet radiation.

Another object of the invention is to provide a sterilization apparatus of the aforementioned character, which includes a substantially UV-C transparent closure cap of novel design for closing the access site and a compact, easy to use irradiating apparatus for controllably irradiating the UV-C transparent closure cap with UV-C radiation, that is, ultraviolet light having a wavelength of between about 200 and about 280 nm.

Another object of the invention is to provide a sterilization apparatus of the class described which includes a small, hand-held irradiation apparatus that can be conveniently used either in the hospital or home care environment.

Another object of the invention is to provide a sterilization apparatus, of the type described in the preceding paragraph, which can be used by caregivers with a minimum amount of training.

Another object of the invention is to provide a sterilization apparatus of the character described which is of simple construction and can be inexpensively produced.

DISCUSSION OF THE INVENTION

Definitions

As used herein the following terms have the following meanings:

"Access Site" means an attachment point for various therapeutic or diagnostic medical devices including, but not limited to, stopcocks, needle-less access sites, IV bags, infusion pumps, drug delivery pumps, kidney dialysis equipment, thermal dilution catheters and like devices.

"UV-C" means ultraviolet light having a wavelength of between about 200 and about 280 nm.

"Germicidal Lamp" means a commercially available UV generating lamp that produces energy output at about 254 nm.

Figure 1:
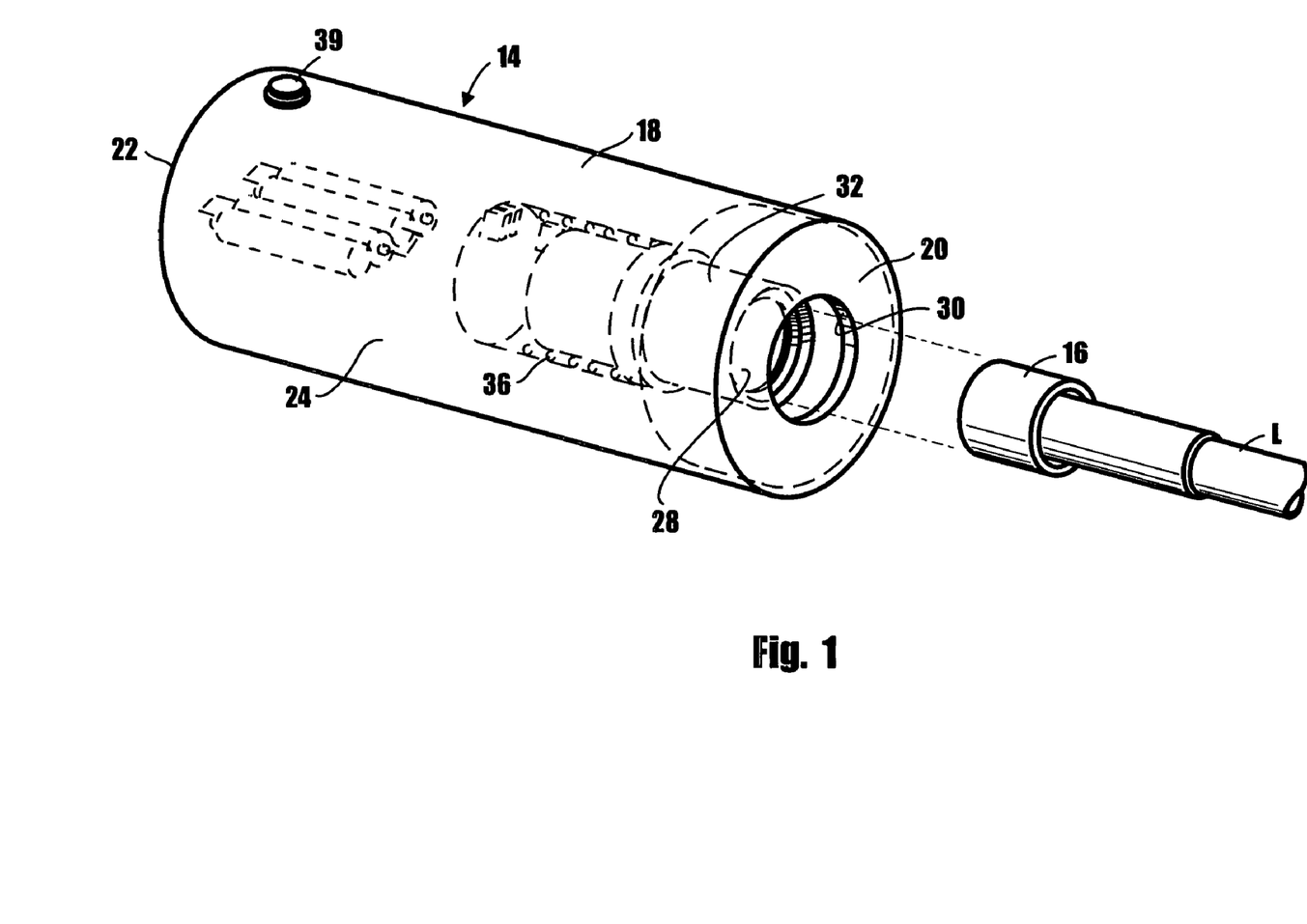
FIG. 1 is a generally perspective view of one form of the sterilization apparatus of the present invention.
Figure 5:
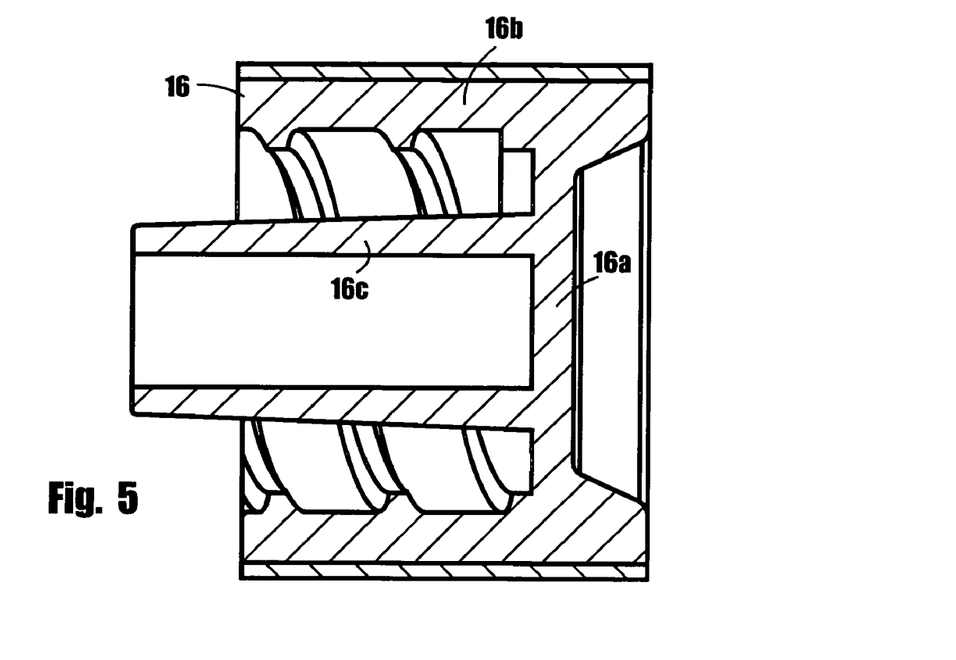
FIG. 5 is a greatly enlarged, longitudinal, cross-sectional view of one form of the UV transparent closure cap of the present invention.
Figure 7:
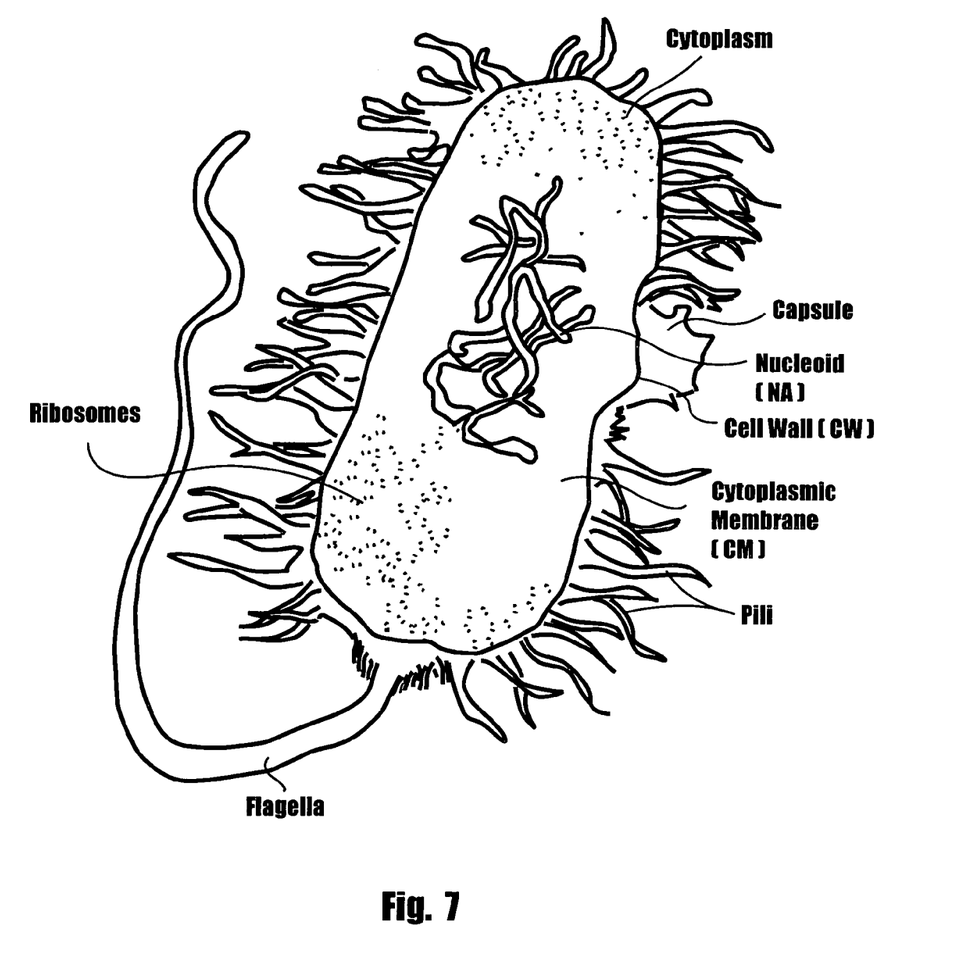
FIG. 7 is a generally diagrammatic view of a typical bacterial cell structure.

Referring to the drawings and particularly to FIGS. 1, 5 and 7, FIG. 1 is a generally perspective view of one form of the sterilization apparatus of the invention; FIG. 5 is an enlarged, longitudinal cross-sectional view of one form of the UV transparent closure cap of the invention and FIG. 7 is a simplified sketch of a bacterial cell.

With regard to the sterilization method of the invention and referring particularly to FIG. 7, the main structures of interest are the cell wall "CW", the cytoplasmic membrane "CM" and the nucleic acid "NA". The target of UV light disinfection is the genetic material or NA (also known as DNA) in the center of the cell. Microbes are destroyed by UV light if it penetrates the cell wall and is absorbed by the nucleic acids. The absorption of UV light by the nucleic acids causes rearrangement of the genetic information, which interferes with the cell's ability to reproduce. A cell that cannot reproduce is considered dead, since it is unable to multiply to infectious numbers within the host. Research into the cell's reaction to UV light has shown that the maximum absorption of UV light by nucleic acid occurs at a wavelength of about 260 nm which is very close to the 254 nm emitted by a conventional germicidal UV lamp.

It is well known that micro-organisms differ in their sensitivity to UV light. This variation may be due to cell wall structure, thickness and composition; to the presence of UV absorbing proteins or due to differences in the structure of the nucleic acids themselves. Therefore, the lethal UV dose is different for each type of micro-organism.

Figure 8:
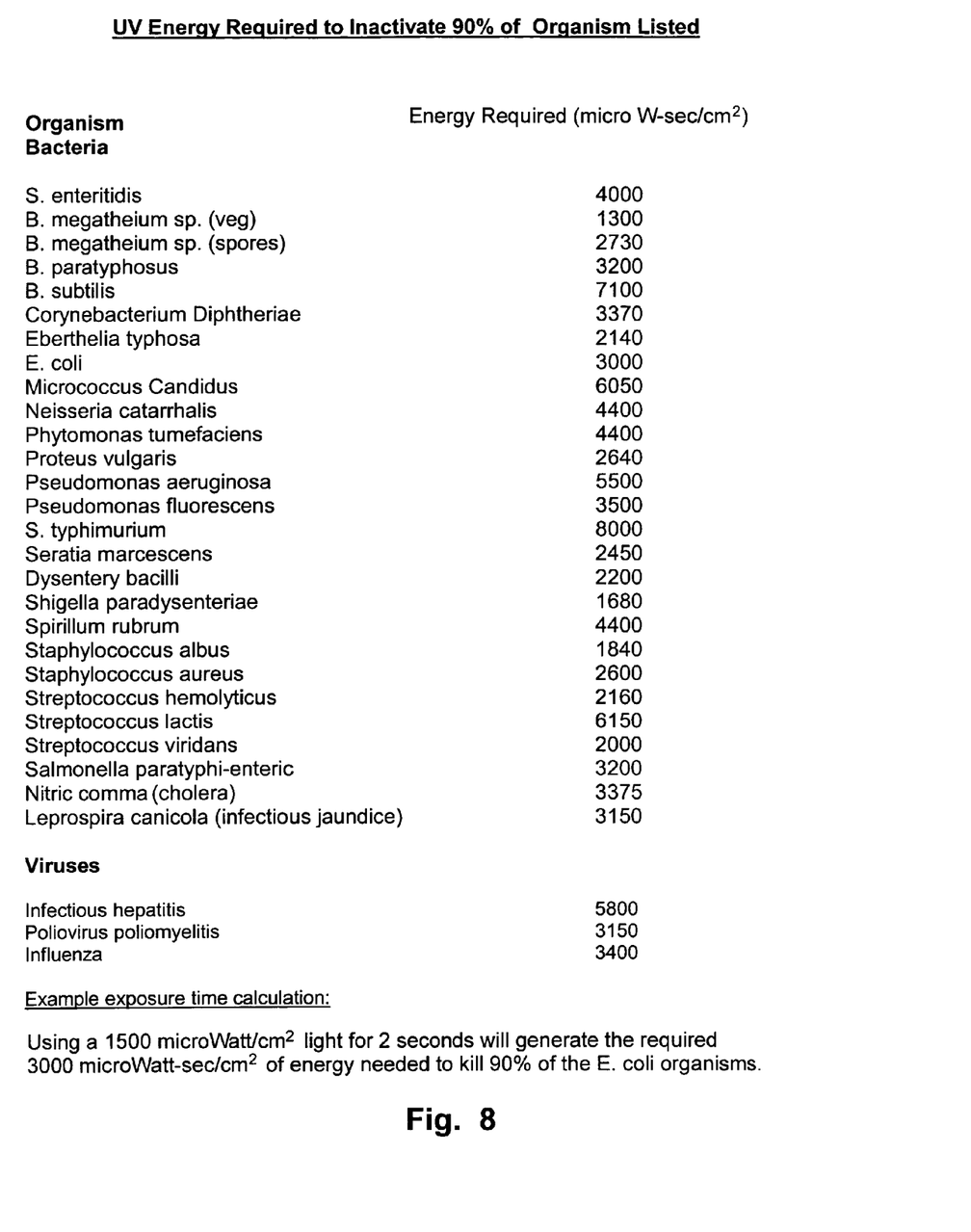
FIG. 8 is a generally tabular representation illustrating the UV energy required to inactivate 90% of the orgasms listed in the representation.

Turning to FIG. 8 of the drawings, this Figure shows the UV energy needed to kill 90% of the population of many common organisms. It is to be noted that a higher kill percentage is possible with more energy output but may not be necessary to achieve significant infection reduction in the hospital.

The dose is a product of the light intensity multiplied by the contact time. Intensity is the amount of UV energy per unit area measured in microwatts per square centimeter. The contact time is the amount of time the microbe is exposed to the UV energy, measured in seconds. Therefore, UV Dose is expressed in microwatt-seconds per square centimeter ($\mu$W-sec/cm$^2$).

Considering now the novel UV transparent cap of the present invention, one form of which is shown in FIG. 5, the present inventors have determined that by coupling the germicidal capabilities of UV-C light with a UV compatible closure device, the caregiver will be able to effectively sterilize the intra-luminal access site before and, if necessary, after opening the portal when attaching diagnostic or therapeutic devices. This constitutes a substantial advance over prior art methods of access site preparation which do not and cannot sterilize both the outer and inner surfaces of an access site.

As will be discussed in greater detail hereinafter, the method of the present invention requires the use of a special, substantially UV transparent cap on each access site instead of the typical prior art plastic, UV-C opaque, 'dead end' caps shown in FIG. 14 and presently in use. In this regard, most materials used for the construction of prior art disposable medical products are UV-C opaque. Only quartz glass and certain varieties of plastics are transparent to UV light in the UV-C range (200-280 nm). Therefore, an important aspect of this invention involves the proper selection of moldable or formable varieties of these materials and similar substantially UV transparent materials, such as various types of polyolefins (for example polyethylene) to assure the appropriate UV-C transparency of the UV transparent cap of the invention. Experience has shown that while complete UV-C transparency of the cap is not necessary, a cap that allows sufficient UV-C energy to pass so that germicidal levels are reached on the target surfaces in less than 30 seconds is desirable.

Turning once again to FIG. 1 of the drawings, one form of the novel sterilization apparatus of the present invention for sterilizing an access site is there illustrated and generally designated by the numeral 14. The apparatus here comprises a substantially UV-C transparent closure cap 16 for closing the access site and irradiating means for controllably irradiating the access site and the substantially UV-C transparent closure cap 16 with UV-C radiation. In the present form of the invention, this important irradiating means comprises a generally cylindrically shaped housing 18 having interconnected front, back, and side walls 20, 22 and 24 respectively. Disposed within housing 18 is a cap receiving chamber 28 that is accessible via an opening 30 formed in front wall 20, which is preferably formed of a UV-C light shielding material, such as a polycarbonate. In the present form of the invention, opening 30 comprises a substantially UV-C transparent portion.

Figure 2:
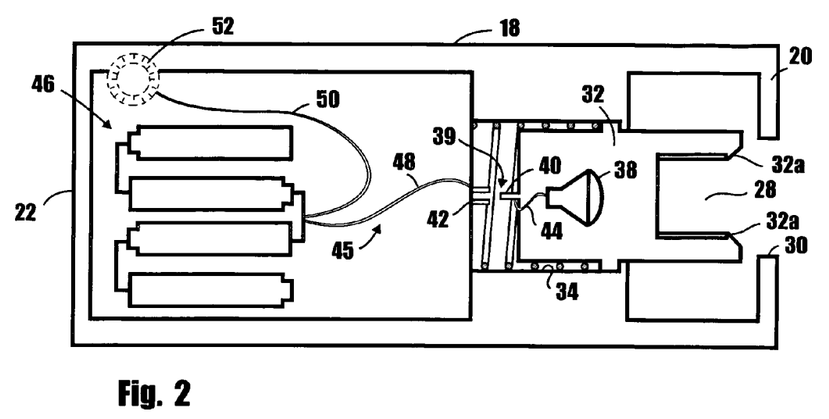
FIG. 2 is a longitudinal, cross-sectional view of the sterilization apparatus shown in FIG. 1.
Figure 3:
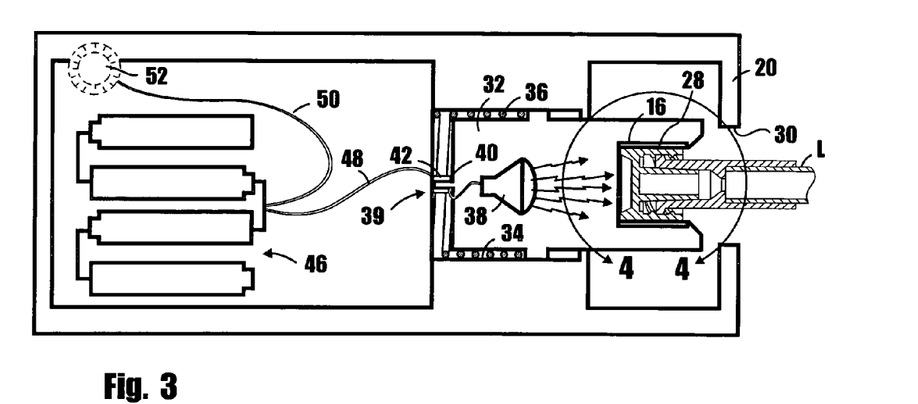
FIG. 3 is a cross-sectional view similar to FIG. 2, but showing the UV transparent closure cap of the invention mated with the sterilization apparatus and illustrating the capture member of the apparatus moved from the first extended position shown in FIG. 2 to the second, inwardly extended position shown in FIG. 3.

As best seen in FIGS. 2 and 3, cap receiving chamber 28 is formed within a capture member 32 that is telescopically moveable within a capture member receiving chamber 34 formed interiorly of housing 18. As indicated in these Figure drawings, capture member 32 is movable between a first extended position shown in FIG. 2 and a second retracted position shown in FIG. 3. Biasing means, shown here as a coil spring 36, which is contained within chamber 34, yieldably resists movement of the capture member 32 toward its retracted position.

Mounted within capture member 32 is a source of UV-C radiation for controllably emitting UV-C radiation in a direction towards cap receiving chamber 28. This source of UV-C radiation is here provided in the form of a commercially available UV generating lamp 38 that produces most of its energy output at about 254 nm. Operably associated with lamp 38 is switching means for energizing the lamp when the capture member 32 reaches its retracted position. This switching means here comprises a switch 39 that comprises a first contact 40 that is carried by capture member 32 and a second contact 42 that is mounted within the capture member receiving chamber 34. Switch 39 is constructed and arranged so that as capture member 32 reaches its inward most position shown in FIG. 3, first contact 40 will engage second contact 42. As indicated in FIG. 2, first contact 40 is connected to lamp 38 by an electrical connector 44 and second contact 42 is connected to a series of operably interconnected batteries 46 by an electrical connector 48. With this construction when first contact 40 engages second contact 42, the circuit 45 will be closed and lamp 38 will be energized.

Also carried by housing 18 is a timer means that is operably associated with switch 42 and lamp 38 by means of an electrical connector 50 for controlling the length of time that the lamp is energized. This timer means is here provided in the form of a conventional, readily commercially available, adjustable timer 52, which forms a part of the electrical circuitry 45 of the invention and can be preset to control the length of time that lamp 38 remains energized after the circuit is closed. Lamp 38, switch 39, batteries 46 and timer 52 are interconnected within the electrical circuitry in a manner well understood by those skilled in the art.

Figure 4:
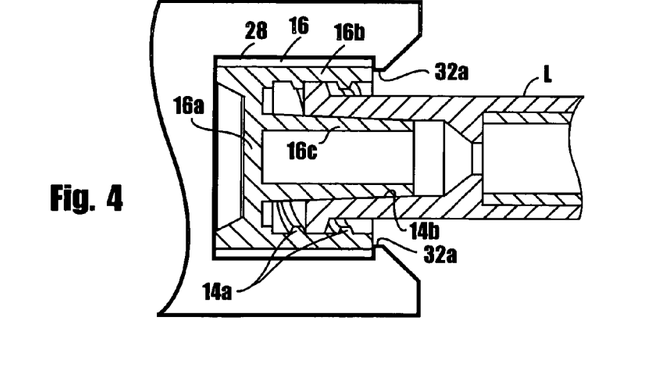
FIG. 4 is a greatly enlarged, fragmentary view of the area designated in FIG. 3 by the numeral 4.

In using the apparatus of the invention to sterilize the access site, the caregiver interconnects the UV-C transparent cap 16 with the access site in the manner illustrated in FIGS. 1, 3 and 4. (In this instance the access site is shown as a conventional IV administration line "L" (see also FIG. 14)).

With respect to the important closure caps of the invention, it is to be noted that, as shown in FIGS. 4 and 5, closure cap 16 comprises a closure wall 16a and an internally threaded skirt portion 16b that is connected to and extends from the closure wall. When cap 16 is interconnected with the access site or administration line "L" in the manner shown in FIG. 4, the internal threads of the skirt portion threadably engage the external threads 14a of the administration line. As the cap is cinched down, the central tapered portion 16c of the cap, which extends from closure wall 16a and is circumscribed by the skirt portion, is sealably received the tapered bore 14b of the administration line to sealably close the inlet of the administration line.

Following the interconnection of the UV-C transparent cap 16 with the access site, the assemblage thus formed is inserted through the opening 30 formed in the front wall 20a of the housing and the cap 16 is guided into the receiving chamber 28 that is formed within a capture member 32. As indicated in FIG. 4, capture member 32 is provided with yieldably deformable locking tabs 32a that are located proximate the mouth of the receiving chamber 28. As the cap 16 is telescopically inserted into the receiving chamber 28, the locking tabs will grip the extremity of the skirt portion 16b in a manner to hold the cap securely in position within the receiving chamber 28.

A continued inward force exerted on the administration line and closure cap will cause the capture member to move into its second, inward position causing the mating of switch contacts 40 and 42 and the concomitant energization of lamp 38. Energization of lamp 38 for the time previously set by the timer 52 will deliver the necessary dose of UV energy onto the outer surface of the cap 16 and through the closure wall 16a into the internal contact surfaces of the access site. This sterilizes the outside surfaces of the cap so that it can be removed cleanly and also sterilizes the inside surfaces that will come in contact with the sterile device that the caregiver is attaching.

By appropriately rotating the administration set relative to the now sterilized cap, the administration line can be removed from the sterilization apparatus and the intervention procedure can be commenced. Once the intervention procedure has been completed, that is, the medication delivered, the blood drawn, or the like, the administration set can be reconnected to the closure cap 16. This done, a second activation of the special UV-C light source would re-sterilize the special UV-C transparent cap, both inside and out.

In practice, the time to sterilize the access site is on the order of just a few seconds and requires only that the caregiver carry the compact, portable sterilization apparatus 14 from patient to patient. This eliminates the troublesome finding and use of the proper alcohol wipes and sterile replacement dead end caps "DE" and results in substantially improved infection control and the effective lowering of infection rates.

Although the largest cost savings to the hospital through the use of the methods and apparatus of the present invention results from the decrease in infection rates, substantial savings also result from the decreased use of sterile "Dead-End" caps and a reduced need for expensive needle-less access valves.

Figure 6:
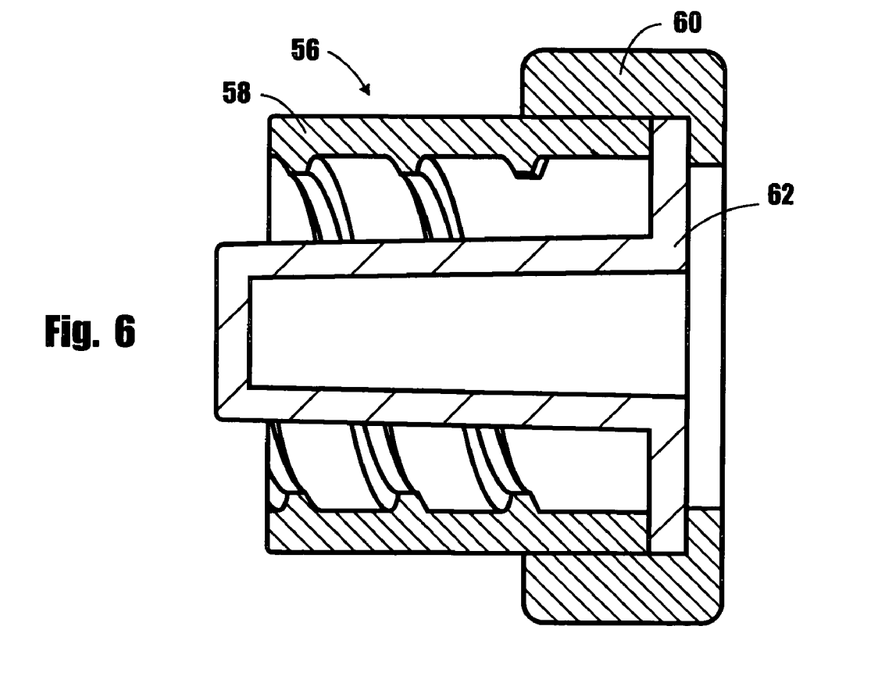
FIG. 6 is a cross-sectional view of still another form of the UV transparent closure cap of the present invention.

Turning to FIG. 6, an alternate form of UV-C transparent closure cap is there shown and generally designated as 56. Unlike the UV-C transparent cap 16 shown in FIG. 5, which is formed in its entirety from UV-C transparent materials, as for example, Teflon, cap 56 comprises a polycarbonate housing 58 that is made up of a generally cylindrical, interiorly threaded body 58 and an annular cap 60. Disposed interiorly of body 58 and held in position by cap 60 is a UV-C transparent, Teflon insert 62. In use, body 58 and an annular cap 60 function to shield the patient from UV-C radiation. UV-C transparent closure cap 56 is used in the same manner for the same purposes as cap 16.

Figure 5A:
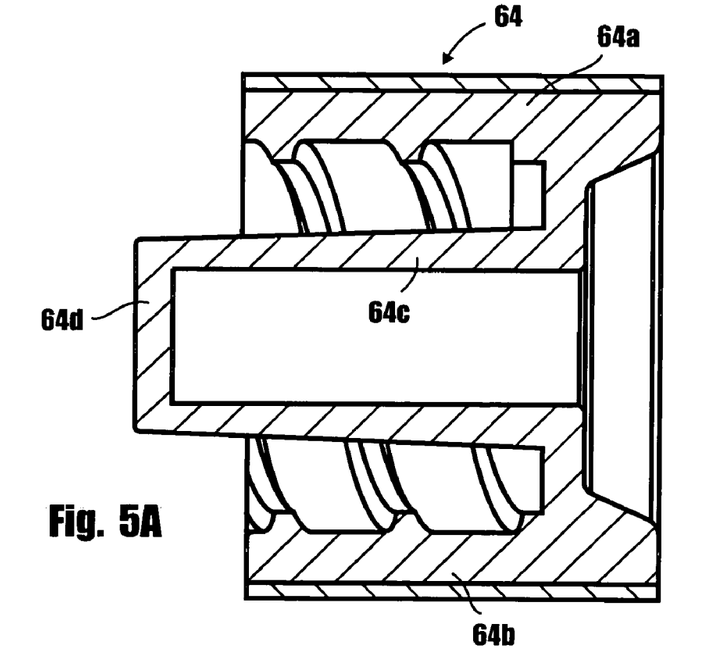
FIG. 5A is a greatly enlarged, longitudinal, cross-sectional view of an alternate form of the UV transparent closure cap of the present invention.

Turning to FIG. 5A of the drawings, still another form of closure cap of the invention is there shown and generally designated by the 64. This closure cap is of similar construction to that shown in FIG. 5 and comprises a closure wall 64a and an internally threaded skirt portion 64b that is connected to and extends from the closure wall. As before, when cap 64 is interconnected with the access site or administration line "L", the internal threads of the skirt portion threadably engage the external threads of the administration line. As the cap is cinched down, the central tapered portion 64c of the cap, which extends from closure wall 64a and is circumscribed by the skirt portion is sealably received by the tapered bore of the administration line to sealably close the inlet of the administration line. However, unlike the previously described cap 16 in which the central tapered portion of the cap was open at its inboard end, the inboard end of cap 64 is closed by a wall 64d, thereby eliminating unwanted dead space.

Figure 6A:
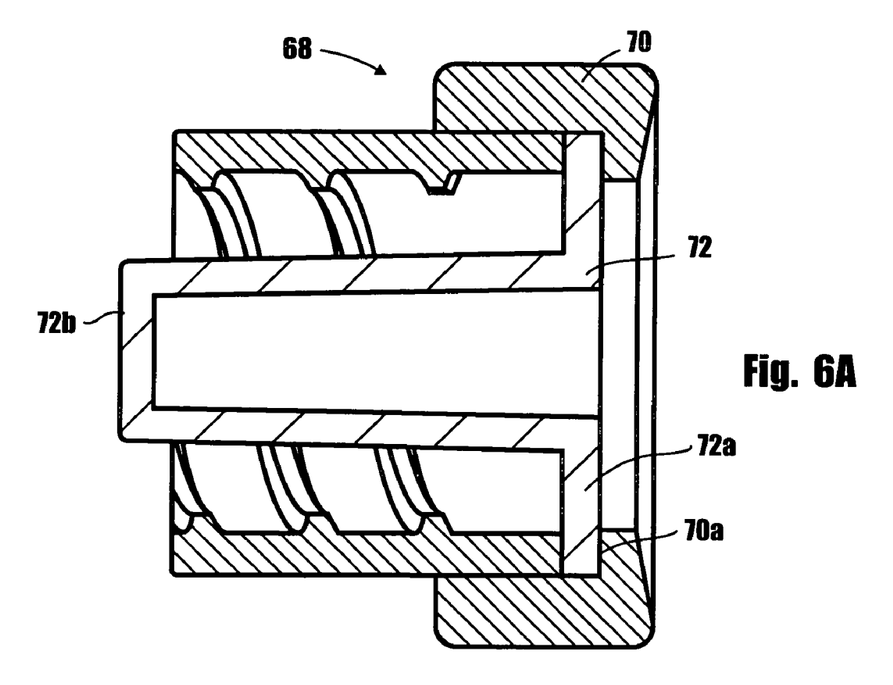
FIG. 6A is a cross-sectional view of yet another form of the UV transparent closure cap of the present invention.

Referring next to FIG. 6A, still another form of UV-C transparent closure cap is there shown and generally designated as 68. Closure cap 68 is similar in some respects to cap 58, but is of a two-piece, rather than three-piece construction. Cap 68 here comprises a one-piece polycarbonate housing 70 that is interiorly threaded. Disposed interiorly of body 70 is a UV-C transparent, Teflon insert 72 having a flange portion 72a and an inwardly extending tapered portion 72b. As shown in FIG. 6A, the peripheral portion of the flange is received with a circumferentially extending groove 70a formed in body 70. As before, body 70 functions to shield the patient from UV-C radiation. UV-C transparent closure cap 68 is used in the same manner for the same purposes as the earlier described cap configurations.

Figure 9:
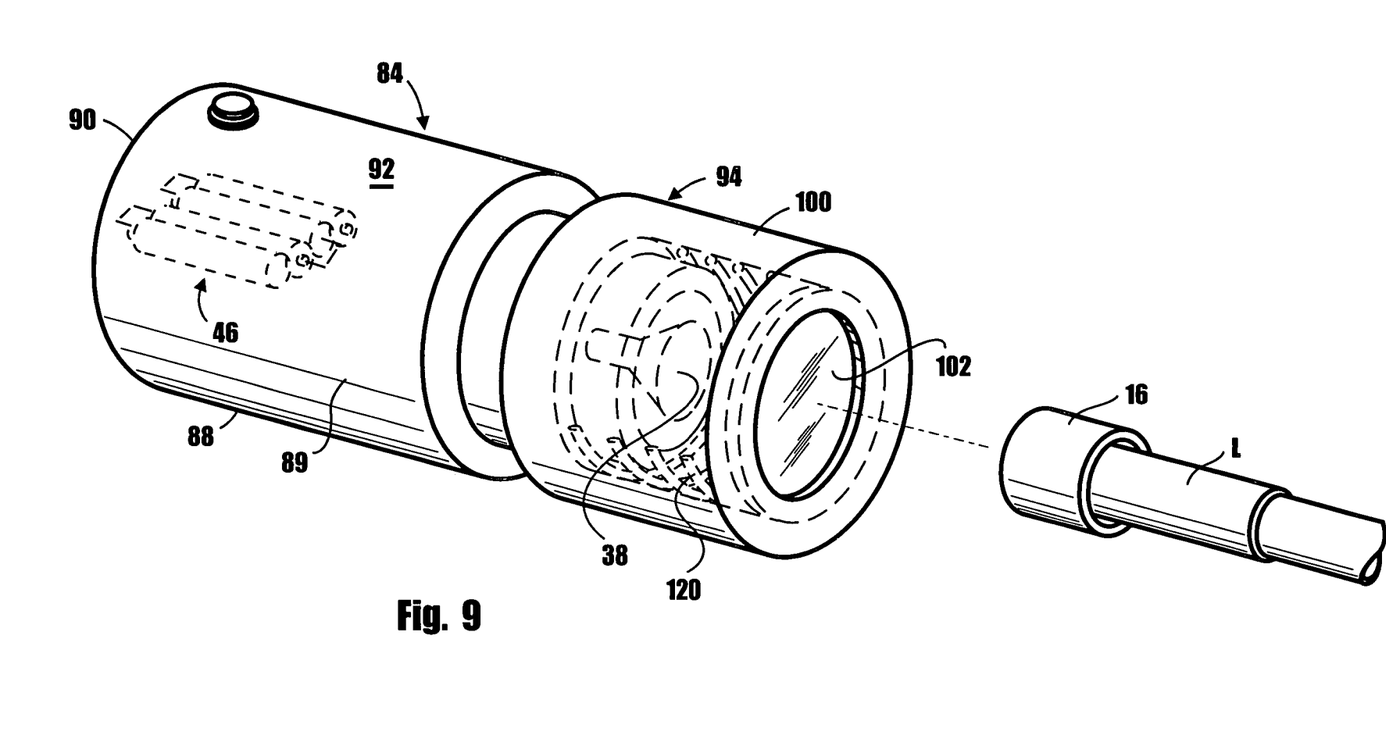
FIG. 9 is a generally perspective view of an alternate form of the sterilization apparatus of the present invention.
Figure 10:
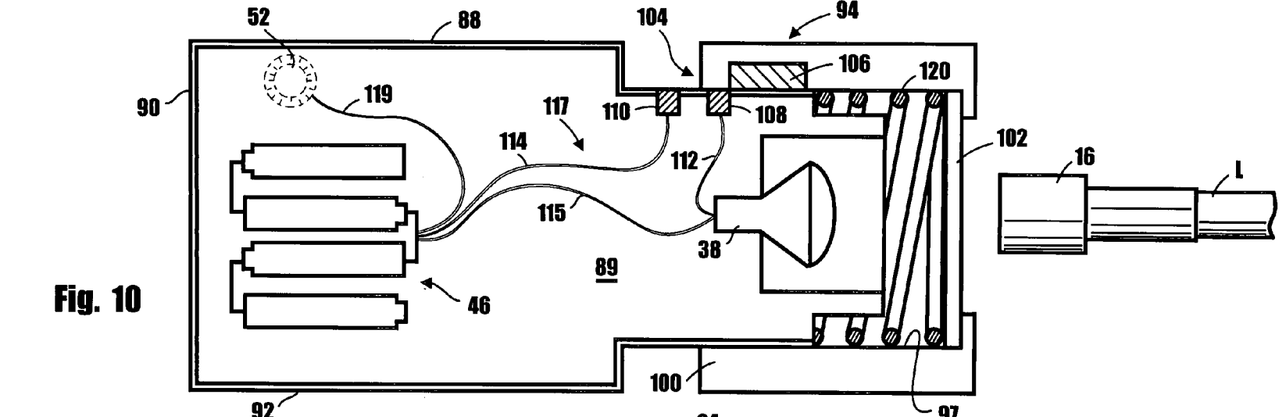
FIG. 10 is a longitudinal, cross-sectional view of the sterilization apparatus shown in FIG. 16.
Figure 11:
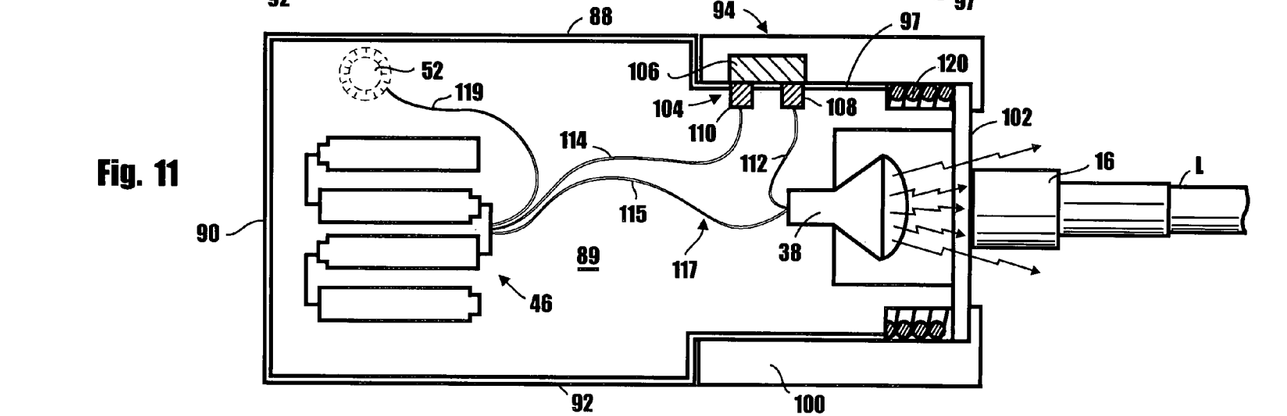
FIG. 11 is a cross-sectional view similar to FIG. 10, but showing the UV transparent closure cap of the invention moved into engagement with the lens of the forward closure assembly of the sterilization apparatus and illustrating the forward closure assembly moved from the first extended position shown in FIG. 10 to the second, retracted position.

Turning next to FIGS. 9, 10 and 11 of the drawings, another form of apparatus for sterilizing an access site is there illustrated and generally designated by the numeral 84. This apparatus is similar in some respects to that shown in FIGS. 1 through 4 and like numerals are used in FIGS. 9, 10 and 11 to identify like components. This latest embodiment of the invention comprises a substantially UV-C transparent closure cap 16, which is identical to that previously described for closing the access site. This alternate form of the sterilization apparatus also includes irradiating means for controllably irradiating the access site and the substantially UV-C transparent closure cap 16 with UV-C radiation. However, the irradiating means, which is of a different construction here comprises a generally cylindrically shaped housing 88 having a hollow chamber 89 that is defined by interconnected back and side walls 90 and 92 and a closure assembly generally designated as 94. Closure assembly 94 is telescopically movable relative to housing 88 between the first extended position shown in FIG. 10 and the retracted position shown in FIG. 11. Closure assembly 94 includes a hollow chamber 97 that is defined by a side wall 100 and a front, UV-C transparent closure lens 102. In this form of the invention closure lens 102 comprises the substantially UV-C transparent portion of the housing.

Back and side walls 90 and 92 of housing 88, as well as side wall 100 of closure assembly 94, are preferably formed of a UV-C light shielding material, such as a polycarbonate.

Mounted within hollow chamber 97 is a source of UV-C radiation for controllably emitting UV-C radiation in a direction towards lens 102. This source of UV-C radiation is once again provided in the form of a commercially available UV generating lamp 38 that produces most of its energy output at about 254 nm. Operably associated with lamp 38 is switching means for energizing the lamp when the closure assembly 94 reaches its retracted position shown in FIG. 11. This switching means here comprises a switch 104 that comprises a first contact 106 that is carried by closure assembly 94 and second and third contacts 108 and 110 that are mounted within housing 88. Switch 104 is constructed and arranged so that as closure assembly 94 reaches its inward most, retracted position shown in FIG. 11, first contact 106 will engage a pair of electrical contacts, namely second and third contacts 108 and 110. As indicated in FIGS. 10 and 11, second contact 108 is connected to lamp 38 by an electrical connector 112 and third contact 110 is connected to a series of operably interconnected batteries 46 by an electrical connector 114. As indicated in the drawings, lamp 38 is connected to batteries 46 by an electrical connector 115. With this construction, when first contact 106 engages the second and third contacts, the circuit 117 will be closed and lamp 38 will be energized.

Also carried by housing 88 is a timer means that is identical in construction and operation to that previously described and functions to control the length of time that the lamp is energized after the circuit is closed. The timer 52 of the timer means is connected batteries 46 by an electrical connector 119.

In using the apparatus of the invention to sterilize the access site, with the assemblage made up of cap 16 and administration line "L" in the position shown in FIG. 10, the caregiver first moves the assemblage forwardly so that the cap 16 engages the lens 102 in the manner shown in FIG. 11. A continued inward pressure on the assemblage will cause the closure assembly 94 to move from the first extended position shown in FIG. 10 into the second retracted position shown in FIG. 11. Biasing means, shown here as a coil spring 120 which is contained within chamber 97, yieldably resists movement of the closure assembly toward its retracted position and will return the closure assembly to its initial position when inward pressure on the cap ceases. As the closure assembly reaches its retracted position, switch 104 will close and the UV lamp 38 will be illuminated and, in the manner previously described, the cap 16 will be exposed to the UV-C radiation for the time period determined by the timer means.

Figure 12:
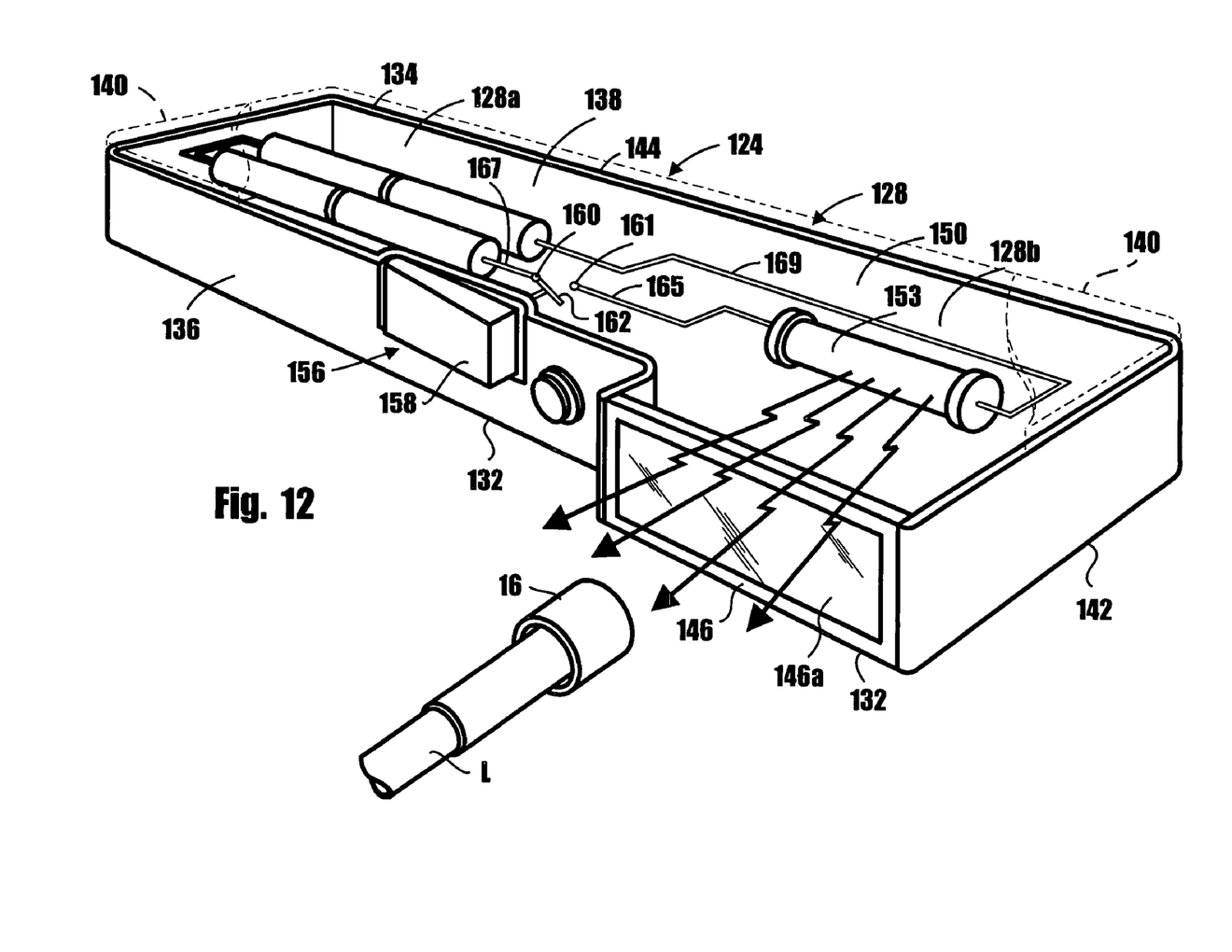
FIG. 12 is a generally perspective view of still another form of the sterilization apparatus of the invention with the top wall removed to show internal construction.
Figure 13:
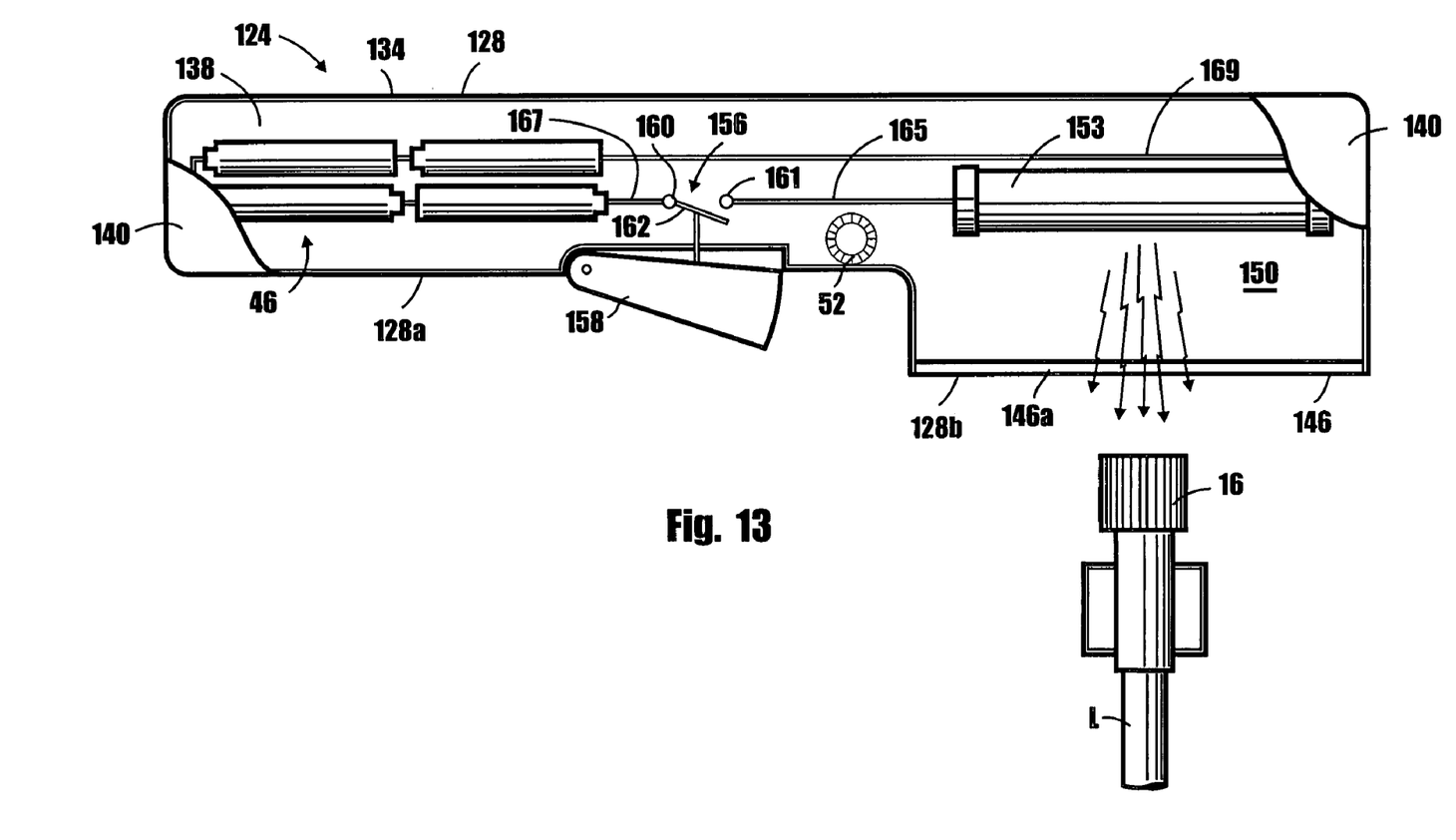
FIG. 13 is a longitudinal view of the sterilization apparatus shown in FIG. 12 with the top wall broken away to show internal construction.

Turning next to FIGS. 12 and 13 of the drawings, yet another form of apparatus for sterilizing an access site is there illustrated and generally designated by the numeral 124. This apparatus is similar in some respects to that shown in FIGS. 9 through 11 and like numerals are used in FIGS. 12 and 13 to identify like components. This latest embodiment of the invention comprises a substantially UV-C transparent closure cap 16, which is identical to that previously described for closing the access site. This alternate form of the sterilization apparatus also includes irradiating means for controllably irradiating the access site and the substantially UV-C transparent closure cap 16 with UV-C radiation. However, the irradiating means, which is of a different construction here comprises a housing 128 having first and second portions 128a and 128b respectively. First portion 128a has interconnected top, bottom, back and front walls 130, 132, 134 and 136 respectively that define an interior chamber 138. Second portion 128b has interconnected top, bottom, back and front walls 140, 142, 144 and 146 respectively that define an interior chamber 150. Front wall 146 includes a UV-C transparent lens portion 146a, which here comprises the substantially UV-C transparent portion of the housing. The various walls of housing 128, save for the lens portion 146a, are preferably formed of a UV-C light shielding material, such as a polycarbonate.

Mounted within chamber 150 is a source of UV-C radiation for controllably emitting UV-C radiation in a direction towards lens portion 146a. This source of UV-C radiation is provided in the form of a differently configured, commercially available, elongated, generally tubular-shaped UV generating lamp 153 that produces most of its energy output at about 254 nm. Operably associated with lamp 153 is switching means for energizing lamp 153. This switching means here comprises a mechanically operated switch assembly 156 that is carried by housing 128. Switch assembly 156 comprises a finger engaging switch member 158 that is pivotally connected to housing 128 for movement between an open position shown in FIG. 13 and an inward, closed position which energizes lamp 153. Switch assembly 156 also includes a pair of contacts 160 and 161 and a contact arm 162 which functions to electrically interconnect the spaced apart contacts. In operating the switch, when the finger engaging switch member 158 is moved into a switch close position lamp 153 is energized.

As indicated in FIG. 13, contact 161 is connected to lamp 153 by an electrical connector 165 and contact 160 is connected to a series of operably interconnected batteries 46 by an electrical connector 167. As illustrated in the drawings, lamp 153 is connected to batteries 46 by an electrical connector 169. With this construction, when switch assembly 156 is closed lamp 153 will be energized.

Also carried by housing 128 is a timer means that is identical in construction and operation to that previously described and functions to control the length of time that the lamp is energized after the circuit is closed.

In using the apparatus of the invention of this latest form of the invention to sterilize the access site, with the assemblage made up of cap 16 and administration line "L" in the position shown in FIG. 13, the caregiver can energize lamp 153 by closing the switch assembly in the manner described in the preceding paragraphs and, in the manner previously described, the cap 16 will be exposed to the UV-C radiation for the time period determined by the timer means.

As previously discussed, and as illustrated in FIGS. 14 through 17, many prior art IV lines and central venous access catheter (CVACs) use some type of molded plastic fitting at their proximal end terminated with a female Luer-lock or Luer-slip connector. In accordance with prior art practices, these connectors are typically closed by a Luer cap when not in use to prevent access site contamination. Each time the line is to be accessed, the Luer cap is removed and discarded as it must be assumed that the outside of the Luer cap is contaminated and that once removed it is nearly impossible to prevent the male Luer configuration from touching a contaminated surface.

Figure 16:
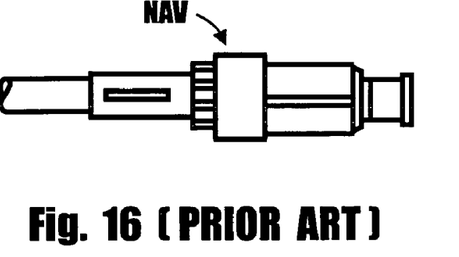
FIG. 16 is a side elevational view of a prior art intravenous line with need-less access valve.
Figure 17:
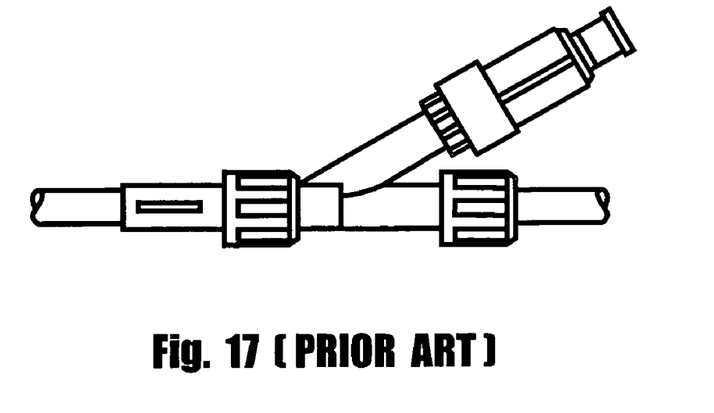
FIG. 17 is a side-elevational view of a prior art intravenous line with Y-access site.

As depicted in FIG. 16, in some cases, the IV access sites have been converted to needle-less access valves "NAV", which incorporate an elastomeric seal that can be opened via the tip of a male Luer connector mounted on a syringe or like device. These needle-less access valves are meant to be cleaned with an alcohol saturated swab before the valve is opened by the sterile male Luer tip of a syringe.

Figure 14:
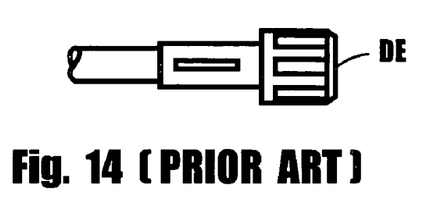
FIG. 14 is a side-elevational view of a prior art intravenous line with standard Luer cap.
Figure 15:
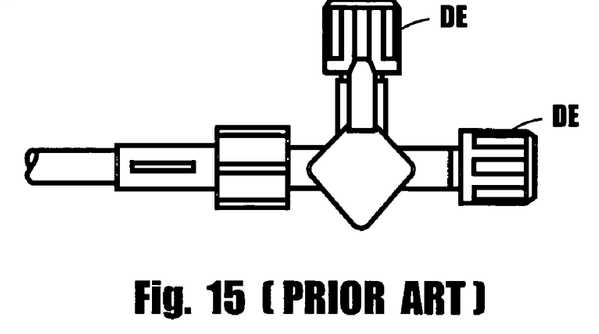
FIG. 15 is a side-elevational view of a prior art intravenous line with stopcock termination.

In accordance with one form of the method of the present invention, the special UV transparent closure caps 16 of the present invention are used on each access site of the character shown in FIGS. 14 and 15 instead of the conventional prior art plastic, UV-C opaque, 'dead end' caps "DE" there shown.

Figure 18:
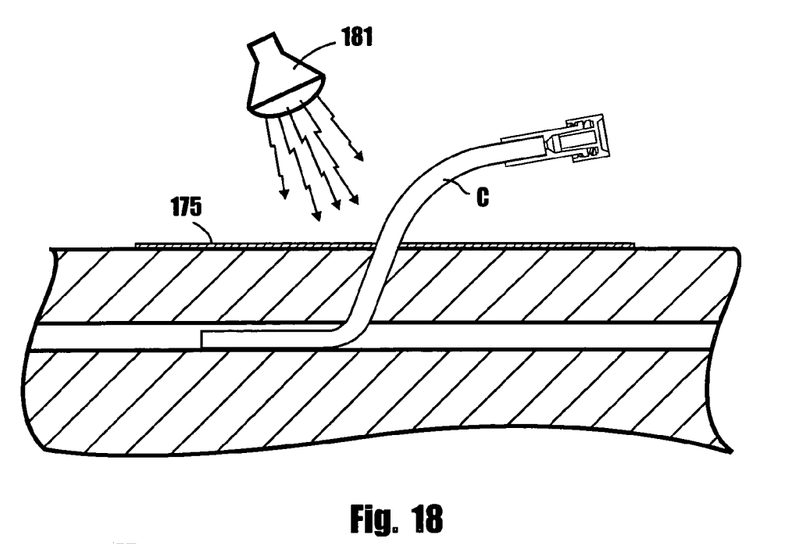
FIG. 18 is a generally diagrammatical, cross-sectional view illustrating an alternate form of the method and apparatus of the present invention making use of the germicidal properties of UV-C light at a catheter puncture site.
Figure 19:
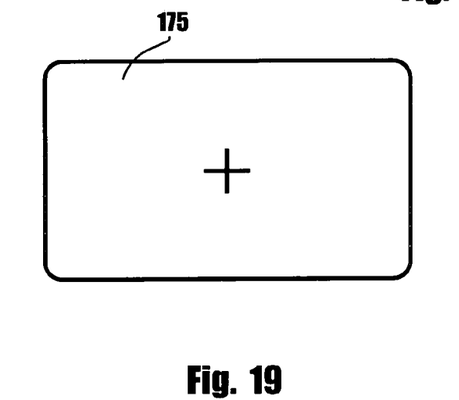
FIG. 19 is a top plan view of one form of UV barrier device of the present invention.
Figure 20:
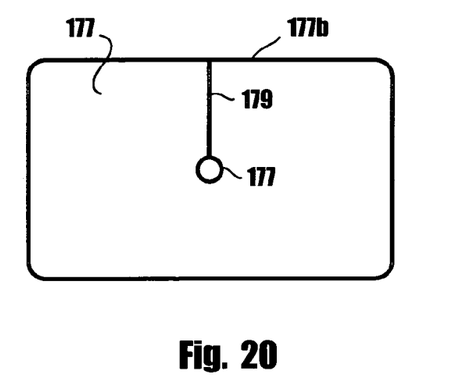
FIG. 20 is a top plan view of an alternate form of UV barrier device of the present invention.

Turning now to FIGS. 18, 19 and 20, another form of the method and apparatus of the invention which makes use of the germicidal properties of the UV-C light at a catheter puncture site is there shown. In order to use the germicidal properties of the UV-C light at the catheter puncture site, it is necessary to apply a protective barrier over the tissue just prior to making the initial puncture for placement of the IV line or central line.

As best seen in FIGS. 18 and 19, the barrier 175 here comprises a thin, flexible, adhesive-backed pad that is constructed from a material that is opaque to UV-C light. Appropriate materials for use in constructing barrier 175 include, but are not limited to, polycarbonate, urethane and various thermoplastic elastomers.

Once the barrier is in place over the catheter puncture site in the manner shown in FIG. 9, the caregiver punctures through the barrier into the appropriate vein or artery leaving the barrier overlaying and protecting the skin around the puncture site. The catheter "C" is then interconnected in a conventional manner as illustrated in FIG. 19 and the IV or central line prepared pursuant to standard operating procedures.

For short term catheters (for example, less than 96 hrs), the UV light barrier 175 would preferably remain in place under the catheter at the skin/catheter junction until the catheter is removed. For longer term catheters, an alternate form of barrier 177 (FIG. 20) is used. As shown in FIG. 20, barrier 177 has a center point 177a and a periphery 177b and is provided with a slit 179 extending from the center point to the periphery that allows it to be conveniently peeled off and replaced as needed without disturbing the catheter.

Periodically, during the patient's hospital stay, a UV-C light source, such as a germicidal lamp 181 is positioned over the skin-catheter junction and activated, thus killing any organisms that have may collected at the skin/catheter junction. During this irradiation step, the barrier that is in place functions to protect the underlying tissue from damage from UV-C irradiation.

Use of the puncture site UV Barrier and the germicidal lamp results in a significant reduction of bloodstream infection rates along with their associated patient mortality and morbidity and provides significant cost savings to the hospital.

Having now described the invention in detail in accordance with the requirements of the patent statutes, those skilled in this art will have no difficulty in making changes and modi- fications in the individual parts or their relative assembly in order to meet specific requirements or conditions. Such changes and modifications may be made without departing from the scope and spirit of the invention, as set forth in the following claims.

We claim:

1. An apparatus for sterilizing an access site comprising a closure cap for closing the access site and irradiating means for controllably irradiating closure cap with UV-C radiation, said closure cap comprising:
   (a) a hollow, substantially UV-C opaque body; and
   (b) a substantially UV-C transparent insert disposed within said body.

2. An apparatus for sterilizing an access site comprising a closure cap for closing the access site, said closure cap having a UV-C transparent portion and irradiating means for controllably irradiating said closure cap with UV-C radiation, said irradiation means comprising:
   (a) a housing having an opening for receiving said closure cap and including an internal chamber and a substantially UV-C transparent portion;
   (b) a source of UV radiation disposed within said housing for emitting UV-C radiation in a direction towards substantially UV-C transparent portion;
   (c) switching means carried by said housing for controllably energizing said source of UV radiation; and
   (d) a connector member disposed within the said housing proximate said opening, said connector member having a cap receiving chamber for receiving therein said closure cap, said cap receiving chamber having gripping means for releasably gripping said closure cap.

3. An apparatus for sterilizing an access site comprising a closure cap for closing the access site, said closure cap having a UV-C transparent portion and comprising a top wall, an internally threaded skirt portion connected to said top wall and an inwardly extending substantially UV transparent tapered portion connected to said top wall, said internally threaded skirt portion at least partially circumscribing said inwardly tapered portion and irradiating means for controllably irradiating said closure cap with UV-C radiation, said irradiation means comprising:
   (a) a housing including an internal chamber and a substantially UV-C transparent portion;
   (b) a source of UV radiation disposed within said housing for emitting UV-C radiation in a direction towards substantially UV-C transparent portion; and
   (c) switching means carried by said housing for controllably energizing said source of UV radiation.

4. An apparatus for sterilizing an access site comprising a closure cap for closing the access site, said closure cap having a UV-C transparent portion and irradiating means for controllably irradiating said closure cap with UV-C radiation, said irradiation means comprising:
   (a) a generally rectangularly shaped housing having a wall and including an internal chamber and a substantially UV-C transparent portion;
   (b) a source of UV radiation disposed within said housing for emitting UV-C radiation in a direction towards substantially UV-C transparent portion; and
   (c) switching means carried by said housing for controllably energizing said source of UV radiation, said switching means comprising a switch member pivotally connected to said wall of said housing.

5. An apparatus for sterilizing an access site comprising a closure cap for closing the access site and irradiating means for controllably irradiating closure cap with UV-C radiation, said irradiating means comprising:
   (a) a housing having an opening for receiving said closure cap, said housing including an internal chamber including gripping means for releasably gripping said closure cap and a substantially UV-C transparent portion; and
   (b) a source of UV radiation disposed within said housing for emitting UV-C radiation in a direction towards said substantially UV-C transparent portion.

* * * * *